(12) United States Patent
Kinsho et al.

(10) Patent No.: US 9,126,923 B2
(45) Date of Patent: Sep. 8, 2015

(54) METHOD FOR PRODUCING (E)-2-ISOPROPYL-5-METHYL-2,4-HEXADIENYL ACETATE

(71) Applicant: SHIN-ETSU CHEMICAL CO., LTD., Tokyo (JP)

(72) Inventors: Takeshi Kinsho, Niigata-ken (JP); Naoki Ishibashi, Niigata-ken (JP); Yoshiyuki Yumoto, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/527,266

(22) Filed: Oct. 29, 2014

(65) Prior Publication Data

US 2015/0119598 A1    Apr. 30, 2015

(30) Foreign Application Priority Data

Oct. 30, 2013    (JP) .................................. 2013-225425

(51) Int. Cl.
| | | |
|---|---|---|
| C07C 67/08 | (2006.01) | |
| C07C 29/147 | (2006.01) | |
| C07C 67/475 | (2006.01) | |
| A01N 31/02 | (2006.01) | |

(52) U.S. Cl.
CPC ................ *C07C 67/08* (2013.01); *A01N 31/02* (2013.01); *C07C 29/147* (2013.01); *C07C 67/475* (2013.01)

(58) Field of Classification Search
CPC .... C07C 29/132; C07C 67/14; C07C 67/333; A01N 31/02
See application file for complete search history.

(56) References Cited

PUBLICATIONS

Zaragoza Dorwald, Side Reactions in Organic Synthesis, 2005,WILEY-VCH Verlag GmbH & Co. KGaA, Weinheim, Preface. p. IX.*
Sugie et al, Applied Entomology and Zoology, Identification of a Sex Pheromone of the Japanese Mealy Bug *Planococcus kruniae* (Kuwana), 2008, pp. 369-375.*
Hinkins et al, Tetrahedron Letters, Identification and Synthesis of the Sex Pheromone of the Vine Mealybug, *Planococcus ficus*, 2001, 42, pp. 1619-1621.*
Matsui et al, Agricultural and Biological Chemistry, New Attempt at the Synthesis of Lavandulol by a Claisen Type Rearrangement, 1968, 32(10), pp. 1246-1249.*
The Total Synthesis of Natural Products, edited by ApSimon, John Wiley & Sons, vol. 7 (1988) 317-320.
Ho, H.-Y. et al., *Identification and Synthesis of the Sex Pheromone of the Passionvine Mealybug, Planococcus minor (Maskell)*, J. Chem. Ecol. 33 (2007) 1986-1996.
Matsui, M. et al., *New Attempt at the Synthesis of Lavandulol by a Claisen Type Rearrangement*, Agric. Biol. Chem., vol. 32, No. 10 (1968) 1246-1249.
Millar, J. G., *Stereospecific synthesis of the sex pheromone of the passionvine mealybug, Planococcus minor*, Tetrahedron Letters 49 (2008) 315-317.
European Search Report for Application No. EP 14 18 9834 dated Mar. 23, 2015.

* cited by examiner

*Primary Examiner* — Paul A Zucker
(74) *Attorney, Agent, or Firm* — Alston & Bird LLP

(57) ABSTRACT

Provided is a simple and efficient method for producing (E)-2-isopropyl-5-methyl-2,4-hexadienyl acetate. More specifically, provided is a method for producing (E)-2-isopropyl-5-methyl-2,4-hexadienyl acetate including the steps of: isomerizing 2-isopropenyl-5-methyl-4-hexenoic acid (1) into (E)-2-isopropyl-5-methyl-2,4-hexadienoic acid (2), reducing thus formed (E)-2-isopropyl-5-methyl-2,4-hexadienoic acid (2) into (E)-2-isopropyl-5-methyl-2,4-hexadienol (3), and acetylating thus formed (E)-2-isopropyl-5-methyl-2,4-hexadienol (3) into (E)-2-isopropyl-5-methyl-2,4-hexadienyl acetate (4),

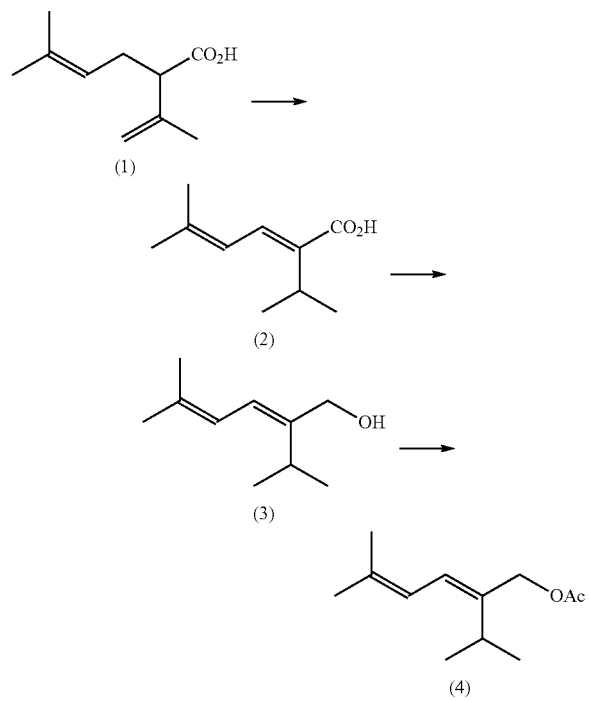

wherein Ac represents an acetyl group.

7 Claims, No Drawings

METHOD FOR PRODUCING (E)-2-ISOPROPYL-5-METHYL-2,4-HEXADIENYL ACETATE

FIELD

The present invention relates to a method for producing (E)-2-isopropyl-5-methyl-2,4-hexadienyl acetate, which is, for example, a sex pheromone of *Planococcus minor* (common name: passionvine mealybug) belonging to mealybug family.

BACKGROUND

Sex pheromones of insects are each a biologically active substance typically released from female individuals and having a function of attracting male individuals. They exhibit high attractive activity even in small amounts. Sex pheromones have been used widely as means for forecasting the emergence or confirming geographical distribution (invasion into a specific area) of insect pests, or means for controlling insect pests. The means for controlling insect pests includes mass trapping, lure & kill or attract & kill, lure & infect or attract & infect, and mating disruption, which have been widely provided in practical use. To utilize sex pheromones, production of a necessary amount of each of the synthetic sex pheromones at a low cost may be needed for basic research and moreover, for application.

*Planococcus minor* (common name: passionvine mealybug, which will hereinafter be abbreviated as "PVMB") is also called Pacific mealybug or Guava mealybug. It is an economically important insect pest because it is widely distributed geographically in the Temperate and Tropical zones and causes damage to many crops. Ho et al. isolated the sex pheromone of this pest insect and determined that it is (E)-2-isopropyl-5-methyl-2,4-hexadienyl acetate (J. Chem. Ecol., 33, 1986-1996 (2007)).

The activity of a sex pheromone is largely influenced by not only the carbon skeleton but also the double bond position or geometry with respect to the structure thereof. In fact, it is reported in the above article by Ho et al. that with respect to the pheromone of PVMB, (Z)-2-isopropyl-5-methyl-2,4-hexadienyl acetate, which is the geometric isomer, inhibits the activity. For fundamental biological research or agricultural research and moreover, for providing for application or practical use, a sufficient amount of synthetic pheromone should be supplied. There is therefore an eager demand for the development of a highly efficient and highly selective production method in which an amount of isomeric byproduct is small so that no purification is required.

Ho et al. have reported the synthesis of the sex pheromone of PVMB. According to the reported synthesis, the intended product is obtained by subjecting ethyl 3-methyl-2-oxobutanoate to three steps, containing a Wittig reaction, a reduction reaction and an esterification reaction, respectively, to obtain a geometric isomer mixture of the intended product and (Z)-2-isopropyl-5-methyl-2,4-hexadienyl acetate, which is the geometric isomer of the intended product; and separating the intended product from the geometric isomer mixture through high-performance liquid chromatography (HPLC) (J. Chem. Ecol., 33, 1986-1996 (2007)).

Millar et al. have reported the synthesis of the sex pheromone of PVMB containing no geometric isomer by starting from a propargylic alcohol compound and using an addition reaction of isopropylmagnesium bromide to form a tri-substituted olefin as a key reaction (Tetrahedron Letters, 49, 315-317 (2008)).

SUMMARY

In the method described in J. Chem. Ecol., 33, 1986-1996 (2007), however, the intermediate after a Wittig reaction has a geometric isomer ratio of 1.3:1, and the geometric isomer is separated from the final product. Since the major product is an unnatural isomer, the method cannot be said to be excellent from the standpoint of selectivity and yield.

The method described in Tetrahedron Letters, 49, 315-317 (2008) is excellent in that the geometric isomer can be obtained selectively, but it is far from an industrial synthesis method because an expensive noble metal catalyst is used for the synthesis of an intermediate, or the intermediate is isolated or purified using silica gel flash chromatography.

It is thus considered to be very difficult to industrially produce a sufficient amount of synthetic pheromone in view of the selectivity or means for isolating or purifying an intermediate or intended product.

The present inventors consider that if (E)-2-isopropyl-5-methyl-2,4-hexadienoic acid can be synthesized, (E)-2-isopropyl-5-methyl-2,4-hexadienyl acetate, the sex pheromone of PVMB, can be industrially produced by reduction and subsequent acetylation of (E)-2-isopropyl-5-methyl-2,4-hexadienoic acid. Further, they expect that (E)-2-isopropyl-5-methyl-2,4-hexadienoic acid can be synthesized because it has an isomeric relationship with relatively easily synthesizable 2-isopropenyl-5-methyl-4-hexenoic acid (lavandulic acid). In addition, (E)-2-isopropyl-5-methyl-2,4-hexadienoic acid, which is an intermediate of the intended product, has a conjugated structure of the carbonyl group (C=O) at the 1-position, a tri-substituted double bond (carbon-carbon double bond C=C) at the 2-position, and tri-substituted double bond at the 4 position so that it is expected to be more stable than the other isomers. The term "double bond" as used herein means a carbon-carbon double bond unless otherwise particularly specified.

The positional and geometric isomerization reactions of the double-bond of an unsaturated carbonyl compound proceed under a various condition such as an acidic, basic, or radical condition and in particular, isomerization from a compound having a double bond not conjugated with a carbonyl group into a compound having a double bond conjugated with a carbonyl group is energetically favorable and proceeds smoothly.

As a result of consideration of the isomerization of 2-isopropenyl-5-methyl-4-hexenoic acid (formula (1) below) used as a starting material into 2-isopropyl-5-methyl-2,4-hexadienoic acid (formula (2) below), the present inventors presume that it is necessary to shift the double bond of the isopropenyl group of 2-isopropenyl-5-methyl-4-hexenoic acid (formula (1) below) which is a β,γ-unsaturated carboxylic acid, to the conjugation side with a carbonyl group for isomerization into 2-isopropylidene-5-methyl-4-hexenoic acid (formula (h) below) which is an α,β-unsaturated carboxylic acid; and it is also necessary to shift the double bond of the isopropylidene group of the α,β-unsaturated carboxylic acid for isomerization into 2-isopropyl-5-methyl-2,4-hexadienoic acid (formulas (j) and (k) below) which is another α,β-unsaturated carboxylic acid. In other words, shift of double bonds has to occur twice successively.

In general, when various positional isomers each having the double bond at the different position, and their geometric isomers each having the (E)-double bond or the (Z)-double bond, or cyclic isomers formed by cyclization which are likely to be taken place particularly under an acidic condition, may be present, an isomerization reaction of double bonds is presumed to form a complex mixture of these isomers, making purification or isolation difficult.

Theoretically possible isomers different in the positions of double bonds and geometric isomers thereof are shown below.

(a)
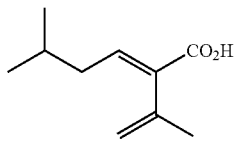

(b)
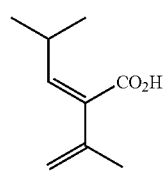

(c)
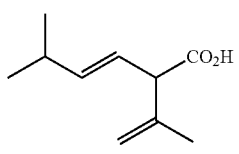

(d)
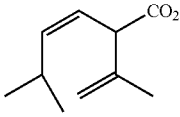

(1)
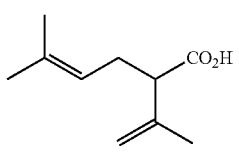

(e)
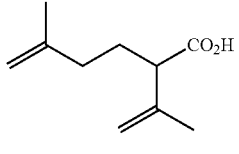

(f)
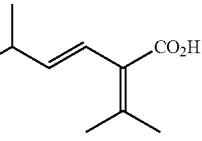

(g)

(h)
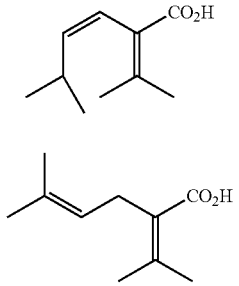

-continued (i)
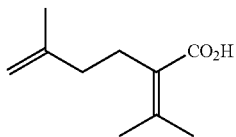

(2)
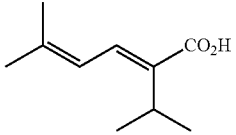

(j)
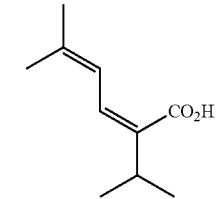

(k)
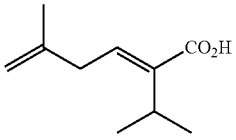

(L)
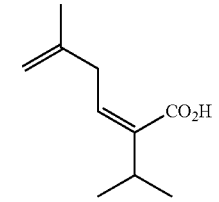

(m)
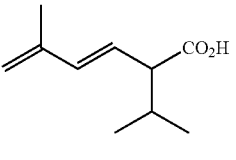

(n)

With the foregoing in view, the invention has been made. An object of the invention is to provide a simple and efficient method for producing (E)-2-isopropyl-5-methyl-2,4-hexadienyl acetate in order to supply a sufficient amount of synthetic pheromone of PVMB that may be needed for use in biological research, agricultural activity test, or practical application or use, or the like.

The present inventors have proceeded with an extensive investigation. As a result, it has been found that isomerization of 2-isopropenyl-5-methyl-4-hexenoic acid under a specific condition can provide a carboxylic acid isomeric mixture containing (E)-2-isopropyl-5-methyl-2,4-hexadienoic acid, and intended (E)-2-isopropyl-5-methyl-2,4-hexadienoic acid can be selectively separated or purified through recrystallization from the carboxylic acid isomeric mixture. It has also been found that by reduction and subsequent acetylation of (E)-2-isopropyl-5-methyl-2,4-hexadienoic acid can industrially produce (E)-2-isopropyl-5-methyl-2,4-hexadienyl acetate, which is the sex pheromone of PVMB, leading to the completion of the invention.

In one mode of the invention, there is provided a method for producing (E)-2-isopropyl-5-methyl-2,4-hexadienyl acetate comprising the steps of: isomerizing 2-isopropenyl-5-methyl-4-hexenoic acid represented by formula (1) into (E)-2-isopropyl-5-methyl-2,4-hexadienoic acid represented by formula (2), reducing (E)-2-isopropyl-5-methyl-2,4-hexadienoic acid (2) into (E)-2-isopropyl-5-methyl-2,4-hexadienol represented by formula (3), and acetylating (E)-2-isopropyl-5-methyl-2,4-hexadienol (3) into (E)-2-isopropyl-5-methyl-2,4-hexadienyl acetate represented by formula (4),

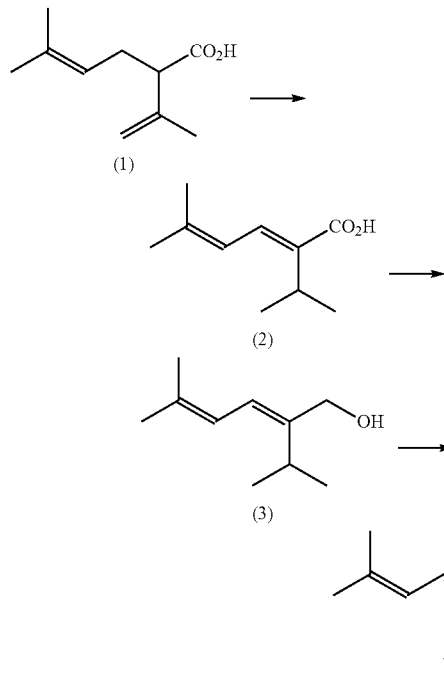

wherein Ac represents an acetyl group.

According to the invention, an industrial production method for selectively and efficiently synthesizing (E)-2-isopropyl-5-methyl-2,4-hexadienyl acetate is provided by using relatively easily synthesizable 2-isopropenyl-5-methyl-4-hexenoic acid as a starting material.

DETAILED DESCRIPTION

The embodiments of the invention will hereinafter be described specifically, but the invention is not limited to or by them.

The starting material is 2-isopropenyl-5-methyl-4-hexenoic acid represented by the following formula (1).

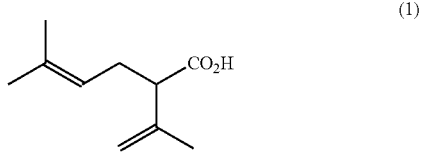

2-Isopropenyl-5-methyl-4-hexenoic acid ester (1) can be synthesized using a method such as the method described in "The Total Synthesis of Natural Products" edited by ApSi-mon, Vol. 7, 317-320, JOHN WILLEY & SONS, (1988) or the method described in the references cited therein. Examples include the method of subjecting 2-methyl-3-buten-2-yl senecioate to Claisen type arrangement under a basic condition to obtain 2-isopropenyl-5-methyl-4-hexenoic acid (Matsui et al., Agric., Biol. Chem., Vol. 32, 1246-1249 (1968)), and the method of alkylating the enolate of senecioic acid ester with a prenyl halide (1-halo-3-methyl-2-butene) to obtain 2-isopropenyl-5-methyl-4-hexenoic acid ester.

Next, the isomerization step of 2-isopropenyl-5-methyl-4-hexenoic acid ester (1) into (E)-2-isopropyl-5-methyl-2,4-hexadienoic acid (2) will be described.

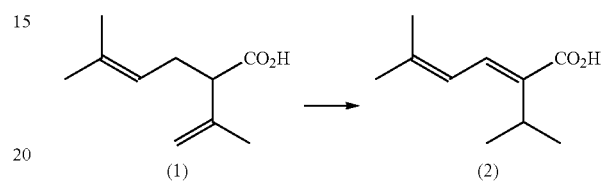

According to the invention, an isomerization reaction (isomerization reaction with respect to the position of a double bond) produces a mixture of, for example, the following isomers.

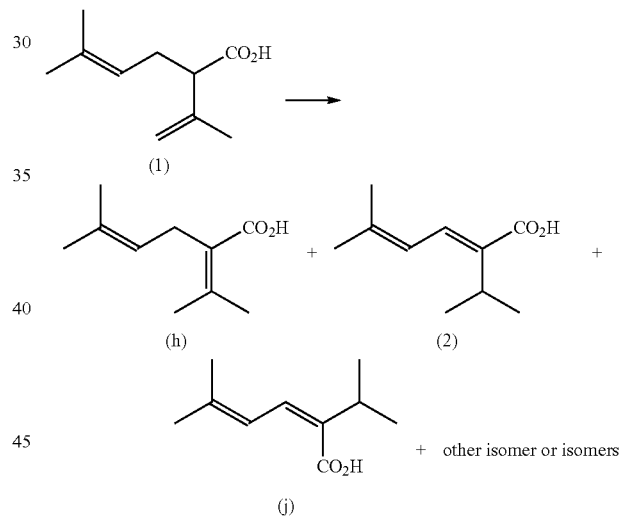

This isomerization reaction is carried out under various reaction conditions such as acidic, basic, or radical conditions. The isomerization reaction under a basic condition using a base is particularly preferable.

Examples of the base to be used for the isomerization reaction include alkoxides (preferably, metal alkoxides, more preferably alkali metal alkoxides) such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide; hydroxide salts (preferably metal hydroxides, more preferably alkali metal hydroxides or alkaline earth metal hydroxides) such as sodium hydroxide, lithium hydroxide, potassium hydroxide, and barium hydroxide; carbonates or bicarbonates (preferably alkali metal carbonates or alkali metal bicarbonates) such as sodium carbonate, potassium carbonate, sodium bicarbonate, and potassium bicarbonate;

organometallic reagents such as methyllithium, ethyllithium, n-butyllithium, methylmagnesium chloride, and dimsylsodium; metal amides such as lithium diisopropylamide, lithium hexamethyldisilazide, sodium hexamethyldisilazide, and lithium dicyclohexylamide; metal hydrides such as sodium hydride, potassium hydride, and calcium hydride; and organic bases such as triethylamine, diisopropylethylamine, tributylamine, N,N-dimethylaniline, N,N-diethylaniline, pyridine, 4-dimethylaminopyridine, quinoline, pyrrolidine, piperidine, collidine, lutidine, morpholine, and piperazine. The base may be used alone or as mixtures of any. The base can be selected in consideration of the type of substrate, reactivity, or selectivity. Among these bases, the alkoxides are particularly preferred.

The amount of the base to be used for the isomerization reaction differs according to the type of the substrate or base. It is preferably from 0.001 mol to a large excess (e.g. from 2 mol to 500 mol), more preferably from 0.1 mol to a small excess (e.g. greater than 1 mol but not greater than 1.5 mol), each per mol of the carboxylic acid compound serving as a substrate. When the reaction proceeds at a sufficiently fast rate, the amount is preferably less than a stoichiometric amount (1 mol), more preferably a catalytic amount (e.g. 0.5 mol or less, or from 0.001 mol to 0.5 mol) from the economical viewpoint.

Examples of the solvent to be used for the isomerization reaction include water; alcohols such as methanol, ethanol, isopropyl alcohol, t-butyl alcohol, benzyl alcohol, methoxyethanol, ethoxyethanol, diethylene glycol monomethyl ether, and triethylene glycol monomethyl ether; ethers such as diethyl ether, di-n-butyl ether, tetrahydrofuran, and 1,4-dioxane; hydrocarbons such as hexane, heptane, benzene, toluene, xylene, and cumene; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); and nitriles such as acetonitrile and propionitrile. The solvent may be used alone or as mixtures of any.

In order to convert the carboxylic acid as the substrate into the intended carboxylic acid in one pot, an aqueous solvent is preferably selected. A water-containing solvent may be selected, or water may be added after isomerization. A combination of water and an alcohol, particularly, a combination of water and a tertiary alcohol is particularly preferable. With regard to the selection of a base and a solvent, the reaction using the alkoxide as the base in the water-containing solvent and the reaction using the hydroxide salt as the base in the alcohol-containing solvent are considered to be similar conditions in the reaction system.

The reaction temperature in the isomerization reaction is preferably from −78° C. to the boiling point of the solvent, more preferably from −10° C. to 100° C. The reaction time can be desirably selected. It is preferable to optimize the reaction time by monitoring the progress of the reaction with gas chromatography (GC) or thin-layer chromatography (TLC). The reaction time of from 5 minutes to 240 hours is typically preferred.

It is presumed that the reaction does not always proceed in an intended direction and a reaction product thus obtained may be an equilibrium mixture of isomers according to the reaction condition. It is therefore preferable to select an appropriate base, solvent and reaction condition from the above-mentioned ones to maximize a ratio of the sum of intended (E)-2-isopropyl-5-methyl-2,4-hexadienoic acid (2) and its (Z) isomer (j) out of the other possible isomers, the latter can be converted into the corresponding (E) isomer in the geometric isomerization of double bond described later.

The intended conversion may be carried out in one pot, or the isomeric mixture obtained by the isomerization reaction may be provided for another isomerization reaction. After a specific isomer is separated from the isomeric mixture obtained by the isomerization reaction, the remaining isomeric mixture may be provided for another isomerization reaction again for recycle. When the starring material, 2-isopropenyl-5-methyl-4-hexenoic acid, is synthesized under a basic condition, the resulting product may be subjected to the isomerization reaction in the system without separation or isolation.

In the invention, if necessary, after a specific isomer is separated from the isomeric mixture obtained by the isomerization reaction, the remaining isomeric mixture may be subjected to another isomerization reaction (geometric isomerization reaction of double bond) again as follows.

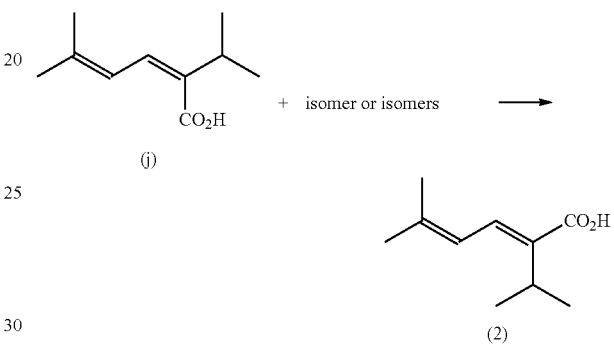

This re-isomerization reaction can be carried out under various reaction conditions such as acidic, basic (including a base to be used in the above-mentioned positional isomerization reaction of double bond), or radical condition. For example, the isomerization reaction using, as a reagent, an elemental chalcogen such as sulfur, selenium or tellurium or a compound thereof; or a compound containing a transition metal element such as ruthenium, iridium, palladium or rhodium is preferred. The isomerization reaction using a sulfur reagent is particularly preferred from the standpoint of reaction efficiency, cost of the reagent, and availability.

A sulfur reagent is typically used and effects the reaction in a solvent or in the absence of solvent, with optional cooling or heating.

Examples of the sulfur reagent include elemental sulfur; inorganic sulfur compounds or salts thereof such as hydrogen sulfide and thiocyanic acid; and organic sulfur compounds or salts thereof such as methanethiol, ethanethiol, butanethiol, benzenethiol, thiosulfuric acid, thioacetic acid, thioglycolic acid, 3-mercaptopropionic acid, diphenyl sulfide, diphenyl disulfide, butadienesulfone, thioacetamide, and thioanisole. The sulfur regent may be used alone or as mixtures of any, and can be selected in consideration of the type of the substrate, reactivity, or selectivity.

The sulfur reagent may be allowed to coexist with a halogen; an azo compound such as azoisobutyronitrile, dimethylazobis(isobutyric acid), or azobis(cyclohexanecarbonitrile); a peroxide such as hydrogen peroxide, di-t-butyl peroxide, benzoyl peroxide, t-butyl hydroperoxide, or methyl ethyl ketone peroxide; or a radical initiator such as triethylborane or diethyl zinc. Of the above-mentioned examples of the sulfur reagent, mercapto-containing compounds and salts thereof, and sulfides are particularly preferred.

The amount of the sulfur reagent differs according to the type of the substrate or the type of the sulfur reagent. It is, for example, from a catalytic amount (e.g. 0.5 mol or less, or from 0.001 mol to 0.5 mol) to a large excess (e.g. from 2 mol to 500 mol), preferably from 0.001 mol to a large excess, more preferably from 0.1 mol to a small excess (e.g. greater than 1 mol but not greater than 1.5 mol), each per mol of the carboxylic acid compound serving as the substrate. When the reaction proceeds at a sufficiently fast rate, the amount is preferably less than a stoichiometric amount from the economical viewpoint. The solvent-free reaction, which means that the reaction is carried out without a solvent, is preferred from the standpoint of economy and high pot yield which means a large amount of product per reaction vessel.

Examples of the solvent to be used in the re-isomerization reaction using a solvent include water; alcohols such as methanol, ethanol, isopropyl alcohol, t-butyl alcohol, benzyl alcohol, methoxyethanol, ethoxyethanol, diethylene glycol monomethyl ether, and triethylene glycol monomethyl ether; ethers such as diethyl ether, di-n-butyl ether, tetrahydrofuran, and 1,4-dioxane; hydrocarbons such as hexane, heptane, benzene, toluene, xylene, and cumene; aprotic polar solvents such as N,N-dimethylformamide (DMF), 1,3-dimethyl-2-imidazolidinone (DMI), dimethyl sulfoxide (DMSO), and hexamethylphosphoric triamide (HMPA); and nitriles such as acetonitrile and propionitrile. The solvent may be used singly or as a mixture of two or more solvents.

The reaction temperature in the re-isomerization reaction is preferably from −78° C. to the boiling point of the solvent, more preferably from room temperature (e.g. from 5° C. to 35° C.) to the boiling point of the solvent. The reaction time can be desirably selected. It is preferable to optimize the reaction time by monitoring the progress of the reaction with gas chromatography (GC) or thin-layer chromatography (TLC). The reaction time of from 5 minutes to 240 hours is typically preferred.

The isomerization with the sulfur reagent is particularly suited for geometric isomerization of double bond. Accordingly, it is preferable to use the isomeric mixture containing (Z)-2-isopropyl-5-methyl-2,4-hexadienoic acid (j) as a substrate and maximize a ratio of intended (E)-2-isopropyl-5-methyl-2,4-hexadienoic acid (2) by selecting an appropriate reagent, solvent, and reaction condition from the above-mentioned ones. The intended conversion may be carried out in one pot, or an isomeric mixture obtained by the isomerization reaction may be provided for another isomerization reaction. After a specific isomer is separated from the isomeric mixture obtained by the isomerization reaction, a remaining isomeric mixture may be provided for the isomerization reaction again for recycle.

An example of the particularly preferable isomerization step includes the isomerization step comprising isomerizing 2-isopropenyl-5-methyl-4-hexenoic acid with a base into the isomeric mixture rich in (E)-2-isopropyl-5-methyl-2,4-hexadienoic acid (2) and (Z)-2-isopropyl-5-methyl-2,4-hexadienoic acid (j) and then isomerizing the isomeric mixture with a sulfur reagent into an isomeric mixture rich in (E)-2-isopropyl-5-methyl-2,4-hexadienoic acid (2).

When the intended intermediate, (E)-2-isopropyl-5-methyl-2,4-hexadienoic acid (2) thus obtained has a sufficient purity, it may be used without purification in the subsequent step. The intended intermediate (E)-2-isopropyl-5-methyl-2,4-hexadienoic acid may be purified from the isomeric mixture. The purification may be carried out by appropriately selecting a method from typical purification methods in organic synthesis such as distillation under reduced pressure, recrystallization and various types of chromatography. Recrystallization is particularly preferred from the standpoint of industrial economy.

The finding by the present inventors that because of excellent crystallinity of (E)-2-isopropyl-5-methyl-2,4-hexadienoic acid, (E)-2-isopropyl-5-methyl-2,4-hexadienoic acid can be isolated from a mixture containing (E)-2-isopropyl-5-methyl-2,4-hexadienoic acid, has greatly contributed to establishment of an industrial production method.

Examples of the solvent to be used for recrystallization include water; alcohols such as methanol, ethanol, isopropyl alcohol, t-butyl alcohol, benzyl alcohol, methoxyethanol, ethoxyethanol, diethylene glycol monomethyl ether, and triethylene glycol monomethyl ether; ethers such as diethyl ether, diisopropyl ether, t-butyl methyl ether, di-n-butyl ether, tetrahydrofuran, and 1,4-dioxane; hydrocarbons such as pentane, hexane, heptane, benzene, toluene, xylene, and cumene; and nitriles such as acetonitrile and propionitrile. The solvent may be used singly or as a mixture of two or more solvents. The recrystallization may be carried out by dissolving an isomeric mixture containing (E)-2-isopropyl-5-methyl-2,4-hexadienoic acid in a solvent selected from the above-mentioned solvents with optional stirring or heating, or the like and then letting the resulting solution stand or cooling the resulting solution for precipitation of crystals. When the isomeric mixture containing (E)-2-isopropyl-5-methyl-2,4-hexadienoic acid is an oil, the "recrystallization" as used herein includes a method of obtaining crystals by adding dropwise, to a poor solvent, a solution in which the oil has been dissolved in a good solvent. The "recrystallization" as used herein also includes a method of obtaining crystals by adding dropwise, to a poor solvent, a solution of crude crystals of the isomeric mixture in a good solvent.

Next, (E)-2-isopropyl-5-methyl-2,4-hexadienoic acid (2) is converted into (E)-2-isopropyl-5-methyl-2,4-hexadienol (3) through a reduction reaction.

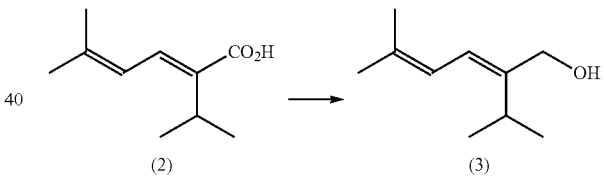

A reduction reaction for converting a carboxylic acid into the corresponding alcohol is applicable for the conversion from (E)-2-isopropyl-5-methyl-2,4-hexadienoic acid (2) into (E)-2-isopropyl-5-methyl-2,4-hexadienol (3). The reduction reaction is effected by allowing a reaction substrate to react with a reducing agent typically in a solvent with optional cooling, heating, or the like.

Examples of the reducing agent include hydrogen; boron compounds such as borane, alkylborane, dialkylborane, and bis(3-methyl-2-butyl)borane; metal hydrides such as dialkylsilane, trialkylsilane, alkylaluminum, dialkylaluminum, sodium hydride, lithium hydride, potassium hydride, and calcium hydride; and complex hydrides and alkoxy or alkyl derivatives thereof such as sodium borohydride, lithium borohydride, potassium borohydride, calcium borohydride, sodium aluminum hydride, lithium aluminum hydride, sodium trimethoxyborohydride, lithium trimethoxyaluminum hydride, lithium diethoxyaluminum hydride, lithium tri-tert-butoxyaluminum hydride, sodium bis(2-methoxyethoxy)aluminum hydride, lithium triethylborohydride, and diisobutylaluminum hydride. The complex hydrides are preferable from the standpoint of reaction condition, ease of work-up, and ease of isolation of a product.

The amount of the reducing agent differs according to the type of the reducing agent used or reaction condition, and the like. The amount is typically and preferably from 0.5 mol to a large excess (e.g. from 2 mol to 500 mol), more preferably from 0.9 mol to 8.0 mol, each per mol of the carboxylic acid as the substrate.

Examples of the solvent to be used in the reduction reaction include water; hydrocarbons such as hexane, heptane, benzene, toluene, xylene, and cumene; ethers such as diethyl ether, dibutyl ether, diethylene glycol diethyl ether, diethylene glycol dimethyl ether, tetrahydrofuran, and 1,4-dioxane; alcohols such as methanol, ethanol, 1-propanol, 2-propanol, ethylene glycol monomethyl ether, and diethylene glycol monomethyl ether; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide. The solvent may be used alone or as mixtures of any.

The solvent to be used in the reduction reaction is selected according to the type of the reducing agent used. For example, when lithium borohydride is used as the reducing agent, the preferable solvent includes ethers, a mixed solvent of ether and alcohol, and a mixed solvent of ether and hydrocarbon, and others. When lithium aluminum hydride is used as the reducing agent, the preferable solvent includes ethers and a mixed solvent of ether and hydrocarbon.

The reaction temperature or the reaction time in the reduction reaction each differs according to the type of the reagent or the type of solvent used. For example, when lithium aluminum hydride in tetrahydrofuran is used as the reducing agent, the reaction temperature is preferably from −78° C. to 50° C., more preferably from −70° C. to 20° C. The reaction time can be desirably selected. It is preferable from the standpoint of a yield to allow the reaction to be completed while monitoring the progress of the reaction with gas chromatography (GC) or thin-layer chromatography (TLC) for completion of the reaction. The reaction time is typically from 0.5 to 96 hours.

Isolation or purification of the intended product, (E)-2-isopropyl-5-methyl-2,4-hexadienol (3) can be carried out using a method selected appropriately from typical purification methods in organic synthesis such as distillation under reduced pressure and various types of chromatography. The distillation under reduced pressure is preferred from the standpoint of industrial economy. When the crude intended product has a sufficient purity, it may be used without purification in the subsequent step.

According to the invention, the final step is for an esterification reaction in which (E)-2-isopropyl-5-methyl-2,4-hexadienol (3) is acetylated into the intended target product, (E)-2-isopropyl-5-methyl-2,4-hexadienyl acetate (4).

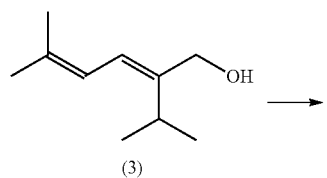

(3)

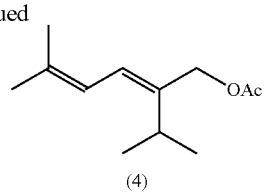

(4)

A method for producing an acetate ester from an alcohol is applicable for this acetylation reaction. Examples of this acetylation reaction include a reaction of (E)-2-isopropyl-5-methyl-2,4-hexadienol (3) with an acetylating agent, a reaction of (E)-2-isopropyl-5-methyl-2,4-hexadienol (3) with acetic acid, an ester exchange reaction between (E)-2-isopropyl-5-methyl-2,4-hexadienol (3) and an acetic acid ester, and a method of converting (E)-2-isopropyl-5-methyl-2,4-hexadienol (3) into the corresponding alkylating agent and then reacting the alkylating agent with acetic acid.

Regarding the reaction of (E)-2-isopropyl-5-methyl-2,4-hexadienol (3) with the acetylating agent, (E)-2-isopropyl-5-methyl-2,4-hexadienol as the reaction substrate is reacted with the acetylating agent in a solvent in the presence of a base or an acid.

Examples of the acetylating agent in the acetylation reaction include acetyl chloride, acetyl bromide, acetic anhydride, mixed acid anhydrides such as: acetic trifluoroacetic anhydride, acetic methanesulfonic anhydride, acetic trifluoromethanesulfonic anhydride, acetic benzenesulfonic anhydride, acetic p-toluenesulfonic anhydride, or p-nitrophenyl acetate. The amount of the acetylating agent is preferably from 1 mol to 40 mol, more preferably from 1 mol to 5 mol, each per mol of the reactant (E)-2-isopropyl-5-methyl-2,4-hexadienol.

Examples of the base to be used in the acetylation reaction include triethylamine, diisopropylethylamine, N,N-dimethylaniline, pyridine, and 4-dimethylaminopyridine. When two or more bases are used, they may be added successively or simultaneously for the reaction.

When the acetylating agent such as acid anhydride is used, the reaction can be carried out, instead of the base, in the presence of an acid selected from inorganic acids such as hydrochloric acid, hydrobromic acid, sulfuric acid, and nitric acid; and organic acids such as oxalic acid, trifluoroacetic acid, methanesulfonic acid, benzenesulfonic acid, and p-toluenesulfonic acid.

Examples of the solvent to be used in the acetylation reaction include chlorine-based solvents such as methylene chloride, chloroform, and trichloroethylene; hydrocarbons such as hexane, heptane, benzene, toluene, xylene, and cumene; ethers such as diethyl ether, dibutyl ether, diethylene glycol diethyl ether, diethylene glycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide, and hexamethylphosphoric triamide. The solvent may be used alone or as mixtures of any.

The reaction temperature of the acetylation reaction can be selected appropriately according to the type of the acetylating agent or reaction condition. In general, it is preferably from −50° C. to the boiling point of the solvent, more preferably from −20° C. to room temperature (e.g. from 5° C. to 35° C.).

Regarding the reaction of (E)-2-isopropyl-5-methyl-2,4-hexadienol (3) with acetic acid, it is a dehydration reaction between an alcohol and a carboxylic acid, and is typically carried out in the presence of an acid catalyst.

The amount of acetic acid to be used in the reaction of (E)-2-isopropyl-5-methyl-2,4-hexadienol (3) with the acetic acid is preferably from 1 mol to 40 mol, more preferably from 1 mol to 5 mol, each per mol of (E)-2-isopropyl-5-methyl-2, 4-hexadienol (3).

Examples of the acid catalyst to be used in the reaction of (E)-2-isopropyl-5-methyl-2,4-hexadienol (3) with acetic acid include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. The acid catalyst may be used alone or as mixtures of any. The amount of the acid catalyst is preferably from 0.001 mol to 1 mol, more preferably from 0.01 mol to 0.05 mol, each per mol of (E)-2-isopropyl-5-methyl-2,4-hexadienol (3).

The solvent to be used in the reaction of (E)-2-isopropyl-5-methyl-2,4-hexadienol (3) with acetic acid includes the same solvents as the solvents exemplified in the above acetylation reaction.

The reaction temperature in the reaction of (E)-2-isopropyl-5-methyl-2,4-hexadienol (3) with acetic acid is, in general, preferably from −50° C. to the boiling point of the solvent, more preferably from room temperature (e.g. from 5° C. to 35° C.) to the boiling point of the solvent. The reaction can proceed while azeotropically removing water formed from the system by using a solvent containing a hydrocarbon such as hexane, heptane, benzene, toluene, xylene, or cumene. In this case, water may be distilled off while refluxing at the boiling point of a solvent under normal pressure, or water may be distilled off at a temperature lower than the boiling point under reduced pressure.

Regarding the ester exchange reaction between (E)-2-isopropyl-5-methyl-2,4-hexadienol (3) and an acetic acid ester, an alkyl acetate is reacted with (E)-2-isopropyl-5-methyl-2, 4-hexadienol (3) in the presence of a catalyst and then the resulting alcohol is removed.

The alkyl acetate to be used in the ester exchange reaction is, for example, preferably a primary alkyl acetate, particularly preferably methyl acetate, ethyl acetate, and n-propyl acetate from the standpoint of cost and ease of reaction proceeding. The amount of the alkyl acetate is preferably from 1 mol to 40 mol, more preferably from 1 mol to 5 mol, each per mol of (E)-2-isopropyl-5-methyl-2,4-hexadienol (3).

Examples of the catalyst to be used in the ester exchange reaction include inorganic acids such as hydrochloric acid, hydrobromic acid, sulfuric acid, and nitric acid; organic acids such as oxalic acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. The catalyst may be used alone or as mixtures of any. The amount of the catalyst is preferably from 0.001 mol to 20 mol, more preferably from 0.01 mol to 0.05 mol, each per mol of (E)-2-isopropyl-5-methyl-2,4-hexadienol (3).

The ester exchange reaction may be carried out in the absence of solvent. The alkyl acetate itself serving as a reaction reagent may be used as a solvent. The solvent-free reaction is preferable because it does not require an extra operation such as concentration or solvent recovery. It is possible to use the solvent as an aid. When a solvent is used in the ester exchange reaction, examples of the solvent include hydrocarbons such as hexane, heptane, benzene, toluene, xylene, and cumene; and ethers such as diethyl ether, dibutyl ether, diethylene glycol diethyl ether, diethylene glycol dimethyl ether, tetrahydrofuran, and 1,4-dioxane. The solvent may be used alone or as mixtures of any.

The reaction temperature for the ester exchange reaction may be selected appropriately according to the type of the alkyl acetate or reaction condition. The ester exchange reaction is typically carried out under heating. Good results can be obtained by carrying out the reaction at a temperature around the boiling point of a low-boiling-point lower alcohol generated during the ester exchange reaction, while removing the lower alcohol thus generated. The lower alcohol includes methanol, ethanol, and 1-propanol. The alcohol may be distilled off under reduced pressure at a temperature lower than the boiling point.

Regarding the method of converting (E)-2-isopropyl-5-methyl-2,4-hexadienol (3) into the corresponding alkylating agent and then reacting the alkylating agent with acetic acid, for example, (E)-2-isopropyl-5-methyl-2,4-hexadienol (3) is converted into the corresponding halide such as chloride, bromide or iodide, or into the corresponding sulfonic acid ester such as methanesulfonic acid ester, trifluoromethanesulfonic acid ester, benzenesulfonic acid ester, or p-toluenesulfonic acid ester; and then, the corresponding halide or sulfonic acid ester is reacted with acetic acid, typically in a solvent, under a basic condition.

The solvent, base, reaction time, and reaction temperature to be used in the method of converting (E)-2-isopropyl-5-methyl-2,4-hexadienol (3) into the corresponding alkylating agent and then reacting the alkylating agent with acetic acid, may be the same as those described in the reaction of (E)-2-isopropyl-5-methyl-2,4-hexadienol (3) with the acetylating agent. Instead of a combination of acetic acid and the base in the ester exchange reaction, an acetate salt such as sodium acetate, lithium acetate, potassium acetate, or ammonium acetate may be used.

The isolation or purification of the intended product, (E)-2-isopropyl-5-methyl-2,4-hexadienyl acetate (4) can be carried out using a method selected appropriately from typical purification methods used in organic synthesis such as distillation under reduced pressure and various types of chromatography. The distillation under reduced pressure is preferable from the standpoint of industrial economy.

In such a manner, a simple and efficient method for producing (E)-2-isopropyl-5-methyl-2,4-hexadienyl acetate, which is the synthetic sex pheromone of PVMB, is provided in order to supply a sufficient amount of the synthetic pheromone necessary for application or use.

EXAMPLES

The invention will hereinafter be described more specifically on basis of Examples and Comparative Examples. It should not be construed that the invention is limited to or by Examples.

The term "purity" as used hereinafter is a value determined by gas chromatography (GC) analysis unless otherwise specifically indicated.

Synthesis Example 1

Synthesis of 2-isopropenyl-5-methyl-4-hexenoic acid (1) as a Starting Material

In a nitrogen atmosphere, a mixture of the 40.3 mmol of sodium hydride, obtained from 1.61 g of a 60% suspension in mineral oil by removal of mineral oil with n-hexane washing, and 50 ml of toluene was heated to reflux with stirring, and then subjected to dropwise addition of 6.76 g of 2-methyl-3-buten-2-yl senecioate having a purity of 96.2% over one hour. After reflux was continued for 80 minutes, 50 ml of diethyl ether was added thereto and 2 ml of methanol was added dropwise thereto. Then, 60 ml of water was added thereto to separate an aqueous phase. The aqueous phase thus separated was acidified by addition of 20% hydrochloric acid, followed by extraction with diethyl ether. The diethyl ether solution was subjected to typical work-up including washing, drying and concentration to obtain 7.69 g of the crude intended product. The yield was 89%.

GC analysis results revealed that the crude product was a 45.7:54.2 mixture of 2-isopropylidene-5-methyl-4-hexenoic acid ($\alpha,\beta$-unsaturated carboxylic acid) and 2-isopropenyl-5-methyl-4-hexenoic acid ($\beta,\gamma$-unsaturated carboxylic acid) and had a purity of 78.0% in total.

Synthesis Example 2

Synthesis of 2-isopropenyl-5-methyl-4-hexenoic acid (1) as a Starting Material

In a nitrogen atmosphere, a mixture of 117 g of hexamethyldisilazane and 600 ml of tetrahydrofuran was cooled with ice, and subjected to dropwise addition of 425 ml of a 1.65M solution of n-butyllithium in n-hexane over one hour, followed by being stirred for 30 minutes. Then, the resulting mixture was cooled to $-60°$ C. while being stirred. A mixture of 118 g of 2-methyl-3-buten-2-yl senecioate having a purity of 97.8% and 100 g of tetrahydrofuran was added dropwise thereto over 75 minutes. After the temperature of the reaction mixture was raised gradually to room temperature, the reaction mixture was stirred for 6 hours and then cooled with ice again. To the ice-cooled mixture was added 286 g of a 10% aqueous solution of sodium hydroxide to separate the aqueous phase. The aqueous phase was subjected to addition of 400 g of 20% hydrochloric acid and then extracted with diethyl ether. The diethyl ether solution was subjected to typical work-up including washing, drying and concentration to obtain 109.1 g of the crude intended product having a purity of 94.6%. The yield was 90%.

GC analysis results revealed that the crude product contained no 2-isopropylidene-5-methyl-4-hexenoic acid ($\alpha,\beta$-unsaturated carboxylic acid) and had a sufficient purity as a starting material. The crude product was used without purification in the subsequent step.

Synthesis Example 3

Synthesis of ethyl 2-isopropenyl-5-methyl-4-hexenoate

In a nitrogen atmosphere, a mixture of 200.01 g of 2-isopropenyl-5-methyl-4-hexenoic acid (1) having a purity of 85.4%, 89.82 g of potassium carbonate, 11.28 g of tetrabutylammonium chloride, and 800 g of toluene was heated to from 95° C. to 100° C., while being stirred, and then 191.8 g of diethyl sulfate was added dropwise thereto over 35 minutes. The reaction mixture was heated continuously for 2 hours, then cooled to room temperature, and subjected to addition of 510 g of water. The toluene solution was separated from the resulting mixture and then subjected to typical work-up including washing, drying and concentration to obtain the crude product. The crude product was distilled under reduced pressure to obtain 193.4 g of the intended product having a purity of 99.7%. The yield was 97%.

Example 1

Synthesis of (E)-2-isopropyl-5-methyl-2,4-hexadienoic acid (2)

(Synthesis Example Through Isomerization Under a Basic Condition)

In a nitrogen atmosphere, a mixture of 145 g of 2-isopropenyl-5-methyl-4-hexenoic acid (1) and 300 ml of tetrahydrofuran was added to a mixture of 106 g of potassium t-butoxide and 800 ml of tetrahydrofuran at room temperature. After stirred for 10 hours under reflux, the reaction mixture was poured into ice water, followed by extraction with n-hexane. The extract was discarded. The aqueous phase was neutralized with 10% hydrochloric acid and extracted with diethyl ether. The diethyl ether solution was subjected to typical work-up including washing, drying and concentration to obtain 135.30 g of crude product. The yield was 93%.

The crude product was recrystallized from 65 g of n-hexane to obtain 45.76 g (yield: 32%) of crystals and 98.64 g (yield: 68%) of a mother liquor. It should be noted that here and hereafter the mother liquor means a concentrate of the filtrate obtained by filtering off the crystals generated by recrystallization. The content of each isomer in the starting material, crude product, crystals and mother liquor was analyzed using capillary GC analysis and gas chromatography-mass spectrometry (GC-MS). The results are shown in Table 1.

GC conditions:
Column: DB-WAX (product of J&W Scientific), 60 m×0.25 ml/min),
Temp: started at 80° C. and increased at a rate of 2.5° C./min to 230° C. Max,
Injection temperature: 230° C.,
Carrier: He having a flow rate of 1 ml/min,
Split ratio: 50:1,
Detector: FID,
Sample: diluted to from 1 to 10% with n-hexane or diethyl ether

TABLE 1

| GC retention time (min) | Isomer | Isomer Content (area %) | | | |
|---|---|---|---|---|---|
| | | Starting material | Crude product | Crystal | Mother liquor |
| 48.54 | A | — | trace | trace | trace |
| 48.95 | B | — | 0.9 | 0.3 | 1.0 |
| 50.85 | C | 100 | 0.8 | 0.2 | 0.7 |
| 51.84 | D | — | 1.1 | 1.1 | 4.5 |
| 53.47 | E | — | 1.1 | 0.4 | 12.4 |
| 53.57 | F | — | 46.6 | 68.4 | 23.5 |
| 54.64 | G | — | 46.7 | 19.6 | 56.2 |

It should be noted that here and hereafter the sum of the isomer contents does not always reach 100% because of minute peaks present in addition to the peaks of major isomers A to G.

Isomer A: Un-Identified Structure of $C_9H_{15}COOH$
GC-MS (EI, 70 eV): 28, 41, 55, 67, 81, 91, 107 (base peak), 125, 135, 153, 168 (M$^+$).

Isomer B: Un-Identified Structure of $C_9H_{15}COOH$
GC-MS (EI, 70 eV): 27, 41, 55, 69 (base peak), 81, 91, 107, 123, 135, 153, 168 (M$^+$).

Isomer C: 2-Isopropenyl-5-methyl-4-hexenoic acid (1) (Starting Material)
GC-MS (EI, 70 eV): 27, 41, 53, 69 (base peak), 81, 100, 111, 125, 135, 150, 168 (M$^+$).

Isomer D: 2-Isopropyl-5-methyl-3,5-hexadienoic acid (m)
GC-MS (EI, 70 eV): 27, 43, 53, 67, 81 (base peak), 91, 111, 126 [(M-$C_3H_6$)$^+$], 153, 168 (M$^+$).

Isomer E: 2-Isopropylidene-5-methyl-4-hexenoic acid (h)
GC-MS (EI, 70 eV): 27, 41, 55, 67, 81, 95, 107 (base peak), 125, 135, 153, 168 (M$^+$).

Isomer F: (E)-2-Isopropyl-5-methyl-2,4-hexadienoic acid (2) (intended intermediate)
GC-MS (EI, 70 eV): 27, 41, 55, 67, 81, 91, 107, 123, 135, 153 (base peak), 168 (M$^+$).

Isomer G: (Z)-2-Isopropyl-5-methyl-2,4-hexadienoic acid (j)
GC-MS (EI, 70 eV): 27, 41, 55, 67, 81, 91, 107, 123, 135, 153 (base peak), 168 (M$^+$).

Example 2

Synthesis of (E)-2-isopropyl-5-methyl-2,4-hexadienoic acid (2)

(Synthesis Example Through Isomerization without Changing the Basic Condition Employed Upon Synthesis of 2-isopropenyl-5-methyl-4-hexenoic acid (1) which is a Starting Material Prepared in the System)

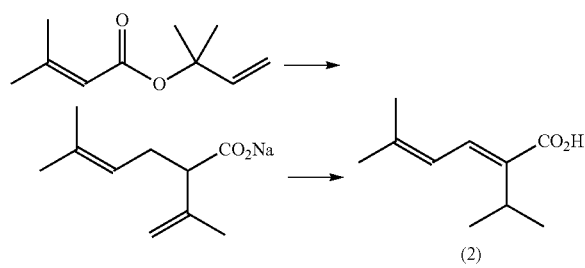

In a nitrogen atmosphere, a mixture of the 125 mmol of sodium hydride, obtained from 5.00 g of a 60% suspension in mineral oil by removal of mineral oil with n-hexane washing, and 30 ml of toluene was heated to reflux with stirring, and subjected to dropwise addition of 20.0 g of 2-methyl-3-buten-2-yl senecioate having a purity of 96.9% over one hour. After reflux was continued for 22 hours, the reaction mixture was cooled to room temperature, and 10 ml of methanol and 40 ml of water were added dropwise thereto. The organic phase was extracted with water and then discarded. The aqueous phases were combined and then made acidic with 20% hydrochloric acid, followed by extraction with diethyl ether. The diethyl ether solution was subjected to typical work-up including washing, drying and concentration to obtain 20.0 g of the crude product having a purity of 3.6% on basis of stoichiometric amount. The content of each isomer in the crude product was analyzed using capillary GC analysis and GC-MS under the similar conditions as in Example 1. The results are shown in Table 2.

TABLE 2

| Isomer *1 | Isomer content (area %) in crude product |
|---|---|
| A | Trace |
| B | Trace |
| C | 33.5 |
| D | 0.8 |
| E | 50.8 |
| F | 3.6 |
| G | 11.1 |

*1: Isomers A to G are the same as those in Table 1.

Example 3

Synthesis of (E)-2-isopropyl-5-methyl-2,4-hexadienoic acid (2)

(Synthesis Example Through Isomerization without Changing the Basic Condition Employed Upon Synthesis of 2-isopropenyl-5-methyl-4-hexenoic acid which is a Starting Material Prepared in the System; and Example of Isolation Through Recrystallization)

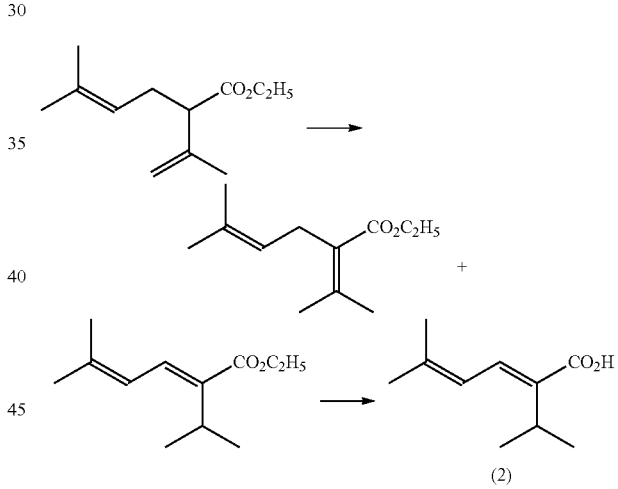

In a nitrogen atmosphere, 3.5 g of potassium t-butoxide was added to a mixture of 38.3 g of a 8.2:81.8 mixture of ethyl 2-isopropenyl-5-methyl-4-hexenoate obtained in Synthesis Example 3 and ethyl 2-isopropylidene-5-methyl-4-hexenoate and 150 ml of tetrahydrofuran at room temperature, and stirred at room temperature overnight. After 60 g of a 25% aqueous solution of sodium hydroxide and 38 g of 99.5% ethanol were added thereto, the resulting mixture was heated to reflux for 7.5 hours with stirring, then subjected to addition of 100 g of a 25% aqueous solution of sodium hydroxide, and refluxed with stirring for further 15 hours. The reaction mixture was poured into ice water, followed by extraction with n-hexane. The extract was discarded. The aqueous phase was neutralized with 10% hydrochloric acid, followed by extraction with diethyl ether. The diethyl ether solution was subjected to typical work-up including washing, drying and concentration to obtain 31.47 g of crude product. The yield was 95.9%.

The crude product was recrystallized from -hexane to obtain 8.72 g (intended product: 85.5% purity, yield: 27%) of Crystal I and 23.16 g (yield: 71%) of Mother liquor I. Crystal I thus obtained was recrystallized again to obtain 4.75 g (intended product: 100% purity, yield: 15%) of Crystal II and 4.05 g (yield: 12%) of Mother liquor II. The content of each isomer in the starting material, crude product, Crystal I, Mother liquor I, Crystal II, and Mother liquor II was analyzed using capillary GC analysis and GC-MS under the similar conditions as in Example 1. The results are shown in Table 3. The starting material in Table 3 is a corresponding ethyl ester. Isomers A to G in Table 3 are the same as those listed in Table 1.

TABLE 3

| | Isomer Content (area %) | | | | | |
|---|---|---|---|---|---|---|
| Isomer *1 | Starting material *2 | Crude product | Crystal I | Mother liquor I | Crystal II | Mother liquor II |
| A | — | 0.4 | Trace | 0.6 | — | — |
| B | — | 1.4 | 0.5 | 1.8 | — | — |
| C | 18.2 | 16.8 | 4.2 | 22.6 | — | 11.4 |
| D | — | 4.7 | 1.0 | 6.2 | — | 0.9 |
| E | 81.8 | 16.9 | 4.0 | 23.1 | — | 10.3 |
| F | — | 48.1 | 85.5 | 30.6 | 100 | 70.6 |
| G | — | 11.6 | 4.8 | 14.1 | — | 5.2 |

*1: Isomers A to G are the same as those in Table 1.
*2: Starting material is a corresponding ethyl ester.

The physical properties and spectrum data of the intended product obtained by recrystallization, which is Crystal II, are shown below.

(E)-2-Isopropyl-5-methyl-2,4-hexadienoic acid (2)

Colorless Crystals
Melting point: 111.3° C.
GC-MS (EI, 70 eV): 27, 41, 55, 67, 81, 91, 107, 123, 135, 153 (base peak) 168 (M$^+$).
IR (D-ATR): ν=2959, 2927, 2870, 2638, 2574, 2516, 1667, 1634, 1586, 1418, 1323, 1273, 995 cm$^{-1}$.
$^1$H-NMR (500 MHz, CDCl$_3$): δ=1.22 (6H, d, J=7.3 Hz), 1.89 (3H, d, J=0.80 Hz), 1.91 (3H, s), 3.02-3.11 (1H, m), 6.26 (1H, dt, J=11.8, 1.2 Hz), 7.50 (1H, d, J=11.8 Hz) ppm.
$^{13}$C-NMR (125 MHz, CDCl$_3$): δ=18.82, 20.93 (2C), 27.05, 27.10, 120.47, 133.13, 135.96, 146.03, 174.07 ppm.

Example 4

Synthesis of
(E)-2-isopropyl-5-methyl-2,4-hexadienoic acid (2)

(Synthesis Example Through Re-Isomerization of an Isomeric Mixture by Using a Base; and Example of Purification and Isolation Through Recrystallization)

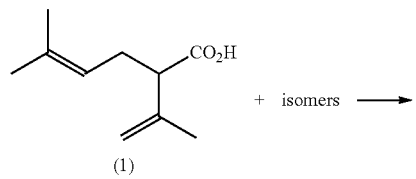

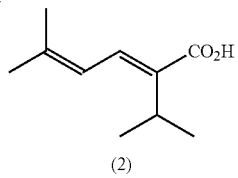

In a nitrogen atmosphere, a mixture of 28.0 g of potassium t-butoxide and 100 ml of tetrahydrofuran was added to a mixture of 21.0 g of an isomeric mixture having a composition shown in Table 4 and containing 30.2% of (E)-2-isopropyl-5-methyl-2,4-hexadienoic acid (2) and 200 ml of tetrahydrofuran, which were being stirred at room temperature. The resulting mixture was heated to reflux for 5 hours while being stirred. After cooled to room temperature, the reaction mixture was poured into ice water, followed by extraction with n-hexane. The extract was discarded. The water phase was neutralized with 10% hydrochloric acid, followed by extraction with diethyl ether. The diethyl ether solution was subjected to typical work-up including washing, drying and concentration to obtain 18.22 g of crude product. The yield was 87%.

The crude product was recrystallized from n-hexane to obtain 1.53 g (intended product: 96.7% purity, yield: 7.3%) of crystals and 14.93 g (yield: 71%) of a mother liquor. The content of each isomer in the starting material, crude product, crystals, and mother liquor was analyzed using capillary GC analysis and GC-MS under the similar conditions as in Example 1 and the results are shown in Table 4.

TABLE 4

| | Isomer Content (area %) | | | |
|---|---|---|---|---|
| Isomer * 1 | Starting material | Crude product | Crystal | Mother liquor |
| A | 0.6 | 0.5 | Trace | 0.1 |
| B | 1.8 | 0.5 | — | 0.6 |
| C | 22.5 | 0.7 | — | 0.4 |
| D | 6.2 | 2.7 | — | 3.1 |
| E | 22.9 | 0.6 | — | 0.6 |
| F | 30.2 | 47.9 | 96.7 | 41.9 |
| G | 13.9 | 46.4 | 3.2 | 51.5 |

*1: Isomers A to G are the same as those in Table 1.

Example 5

Synthesis of
(E)-2-isopropyl-5-methyl-2,4-hexadienoic acid (2)

(Synthesis Example Through Re-Isomerization of a Recycled Isomeric Mixture in the Presence of Base)

In a nitrogen atmosphere, 25.0 g of potassium t-butoxide was added at room temperature to a mixture of 4.00 g of the mother liquor obtained in Example 1, having the content of each isomer shown in Table 5, and 20 ml of tetrahydrofuran. The reaction mixture was heated to reflux for 12 hours, while being stirred. After cooled to room temperature, the reaction mixture was poured into ice water, followed by extraction with n-hexane. The extract was discarded. The aqueous phase was neutralized with 10% hydrochloric acid, followed by extraction with diethyl ether. The diethyl ether extract was subjected to typical work-up including washing, drying and concentration to obtain 3.73 g of a crude product. The yield was 93%. The content of each isomer in the starting material and crude product was analyzed using capillary GC analysis and GC-MS under the similar conditions as in Example 1 and the results are shown in Table 5.

TABLE 5

| Isomer *1 | Isomer Content (area %) | |
|---|---|---|
| | Starting material | Crude product |
| A | Trace | 0.1 |
| B | 1.0 | 1.1 |
| C | 0.7 | 0.7 |
| D | 4.5 | 4.3 |
| E | 12.4 | 1.5 |
| F | 23.5 | 47.3 |
| G | 56.2 | 44.5 |

*1: Isomers A to G are the same as those in Table 1.

Example 6

Synthesis of (E)-2-isopropyl-5-methyl-2,4-hexadienoic acid (2)

(Synthesis Example of Re-Isomerization of an Isomeric Mixture in the Presence of Base)

In a nitrogen atmosphere, 15.0 g of a 25% aqueous solution of sodium hydroxide was added at room temperature to a mixture of 10.0 g of isomeric mixture obtained in the same manner as in Example 2, having the content of each isomer shown in Table 6, and 40 ml of 99.5% ethanol. The reaction mixture was heated to reflux for 18 hours while being stirred, and then cooled to room temperature. The reaction mixture was concentrated under reduced pressure to distill off ethanol, and poured into ice water, followed by extraction with n-hexane. The extract was discarded. The aqueous phase was neutralized with 10% hydrochloric acid, followed by extraction with diethyl ether. The diethyl ether solution was subjected to typical work-up including washing, drying and concentration to obtain 9.46 g of the crude product. The yield was 95%. The content of each isomer in the starting material and crude product was analyzed using capillary GC analysis and GC-MS under the similar conditions as in Example 1. The results are shown in Table 6.

TABLE 6

| Isomer *1 | Isomer Content (area %) | |
|---|---|---|
| | Starting material | Crude product |
| A | Trace | 1.8 |
| B | Trace | 0.3 |
| C | 24.0 | 23.0 |
| D | Trace | 1.6 |
| E | 43.7 | 41.2 |
| F | 15.6 | 16.9 |
| G | 12.6 | 14.6 |

*1: Isomers A to G are the same as those in Table 1.

The contents of the intended (E)-2-isopropyl-5-methyl-2,4-hexadienoic acid (2) and geometric isomer thereof did not increase too much, or the progress of the reaction was very slow. Thus, it is evident from the results that selection of the type of reagent or condition to be used for the isomerization reaction is important.

Example 7

Synthesis of (E)-2-isopropyl-5-methyl-2,4-hexadienoic acid (2)

(Example of Purification and Isolation Through Recrystallization of an Isomeric Mixture)

In a nitrogen atmosphere, 14.93 g of the mother liquor obtained in Example 4, having the content of each isomer shown in Table 7, was recrystallized from 50 ml of isopropyl alcohol to obtain 0.25 g (yield: 2%) of crystals and 14.18 g (yield: 95%) of a mother liquor. The content of each isomer in the starting material, crystals, and mother liquor was analyzed through capillary GC analysis and GC-MS under the similar conditions as in Example 1. The results are shown in Table 7.

TABLE 7

| Isomer *1 | Isomer Content (area %) | | |
|---|---|---|---|
| | Starting material | Crystals | Mother liquor |
| A | 0.1 | — | — |
| B | 0.6 | — | 0.6 |
| C | 0.4 | — | 0.4 |
| D | 3.1 | — | 3.1 |
| E | 0.6 | — | 0.6 |
| F | 41.9 | 96.1 | 41.3 |
| G | 51.5 | 3.9 | 52.8 |

*1: Isomers A to G are the same as those in Table 1.

Example 8

Synthesis of (E)-2-isopropyl-5-methyl-2,4-hexadienoic acid (2)

(Synthesis Example Through Isomerization with a Sulfur Reagent)

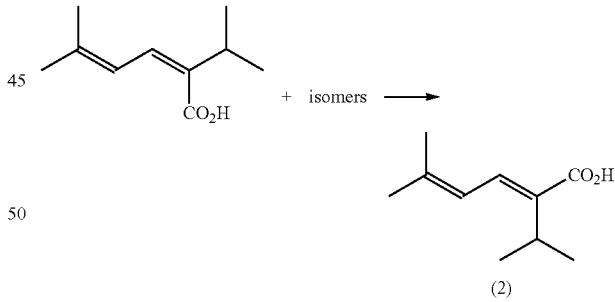

In a nitrogen atmosphere, a mixture of 131.1 g of an isomeric mixture having the content of each isomer shown in Table 8 and containing (E)- and (Z)-2-isopropyl-5-methyl-2,4-hexadienoic acids and 2.17 g of benzenethiol was heated to from 100° C. to 120° C. for 11 hours while being stirred. The reaction mixture was returned to room temperature to obtain crude crystal. The crude crystal was recrystallized from 80 g of n-hexane to obtain 64.5 g (yield: 49%) of Crystal 1 and 66.42 g (yield: 51%) of Mother liquor I. Crystal I was recrystallized from 100 g of diisopropyl ether to obtain 37.18 g (yield: 28%) of Crystal II and 30.40 g (yield: 23%) of Mother liquor II.

The content of each isomer in the starting material, reaction mixture, Crystal I, Mother liquor I, Crystal II, and Mother liquor II was analyzed using capillary GC analysis and GC-MS under the similar conditions as in Example 1. The results are shown in Table 8.

TABLE 8

| Isomer *1 | Isomer Content (area %) | | | | | |
|---|---|---|---|---|---|---|
| | Starting material | Reaction mixture | Crystal I | Mother liquor I | Crystal II | Mother liquor II |
| A | — | — | — | — | — | — |
| B | 1.0 | 1.0 | 0.4 | 1.6 | — | 1.1 |
| C | 0.9 | 0.8 | 0.3 | 1.3 | — | 0.9 |
| D | 4.4 | 3.1 | 1.0 | 4.9 | — | 3.5 |
| E | 1.4 | 1.4 | 0.4 | 2.1 | — | 1.5 |
| F | 40.9 | 71.6 | 89.3 | 47.3 | 97.6 | 69.5 |
| G | 51.5 | 21.3 | 8.6 | 28.5 | 2.4 | 23.5 |

*1: Isomers A to G are the same as those in Table 1.

Example 9

Synthesis of (E)-2-isopropyl-5-methyl-2,4-hexadienoic acid (2)

(Synthesis Example Through Re-Isomerization of an Isomeric Mixture with a Sulfur Compound; and Example of Purification and Isolation of Isomeric Mixture Through Recrystallization)

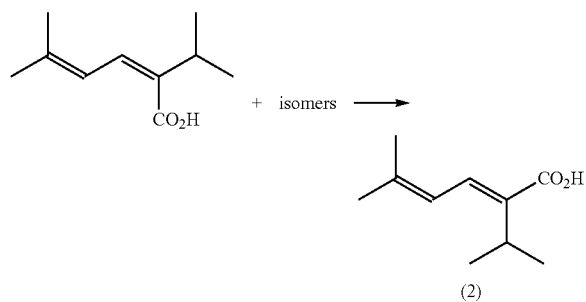

In a nitrogen atmosphere, a mixture of 100.5 g of an isomeric mixture having the content of each isomer shown in Table 9 and containing (E)-2-isopropyl-5-methyl-2,4-hexadienoic acid and (Z)-2-isopropyl-5-methyl-2,4-hexadienoic acid (2) obtained by mixing the crude product obtained in Example 5 with Mother liquors I and II obtained in Example 8, and 0.5 g of benzenethiol was heated to 110° C. for 7.5 hours while being stirred. The reaction mixture was returned to room temperature to obtain crude crystal. The crude crystal was recrystallized from a mixture of 70 ml of n-hexane and 20 ml of diisopropyl ether to obtain 48.49 g (yield: 48%) of crystals and 53.96 g (yield: 54%) of a mother liquor. The content of each isomer in the starting material, reaction mixture, crystal, and mother liquor was analyzed using capillary GC analysis and GC-MS under the similar conditions as in Example 1. The results are shown in Table 9.

TABLE 9

| Isomer *1 | Isomer Content (area %) | | | |
|---|---|---|---|---|
| | Starting material | Reaction mixture | Crystal | Mother liquor |
| A | — | — | — | — |
| B | 1.4 | 1.4 | 0.8 | 2.4 |
| C | 1.0 | 1.0 | 0.5 | 2.2 |
| D | 3.7 | 2.9 | 1.6 | 5.3 |
| E | — | 2.0 | — | 3.1 |
| F | 63.6 | 72.8 | 85.3 | 59.2 |
| G | 27.2 | 19.3 | 10.8 | 27.7 |

*1: Isomers A to G are the same as those in Table 1.

Example 10

Synthesis of (E)-2-isopropyl-5-methyl-2,4-hexadienoic acid (2)

(Example of Purification and Isolation of an Isomeric Mixture Through Recrystallization)

The 41.29 g of an isomeric mixture having the content of each isomer shown in Table 10 and containing (E)- and (Z)-2-isopropyl-5-methyl-2,4-hexadienoic acids was recrystallized from diisopropyl ether to obtain 11.03 g (yield: 27%) of Crystal 1 and 29.07 g (yield: 70%) of Mother liquor I. The Mother liquor I was recrystallized from diethyl ether to obtain 3.50 g (yield from starting material: 9%) of Crystal II and 25.38 g (yield from starting material: 62%) of Mother liquor II. The content of each isomer in the starting material, Crystal I, Mother liquor I, Crystal II, and Mother liquor II was analyzed using capillary GC analysis and GC-MS under the similar conditions as in Example 1. The results are shown in Table 10.

TABLE 10

| Isomer *1 | Isomer Content (area %) | | | | |
|---|---|---|---|---|---|
| | Starting material | Crystal I | Mother liquor I | Crystal II | Mother liquor II |
| A | — | — | — | — | Trace |
| B | 0.4 | — | 0.5 | 0.1 | 0.6 |
| C | 0.3 | — | 0.6 | 0.1 | 0.7 |
| D | 0.8 | — | 1.6 | 0.3 | 1.8 |
| E | 0.4 | — | 0.8 | 0.1 | — |
| F | 76.2 | 98.2 | 67.9 | 93.5 | 64.4 |
| G | 21.0 | 1.8 | 28.2 | 5.9 | 31.3 |

*1: Isomers A to G are the same as those in Table 1.

Example 11

Synthesis of (E)-2-isopropyl-5-methyl-2,4-hexadienol (3)

In a nitrogen atmosphere, a mixture of 48.1 g of 2-isopropyl-5-methyl-2,4-hexadienoic acid (2) having a purity of 98.0% and an (E)-isomer purity of 98.1% and 300 ml of tetrahydrofuran was added dropwise to a mixture of 20.0 g of lithium aluminum hydride and 500 ml of tetrahydrofuran over 70 minutes, which was stirred under ice cooling. The reaction mixture was stirred under ice cooling for 30 minutes and then stirred at room temperature for 17.5 hours, and subjected to careful and sequential additions of 50 g of ethyl acetate, 20.7 g of water, 12.42 g of 25% aqueous sodium hydroxide solution, and 70.38 g of water. The crystals thus formed were filtered. The filtrate was dried and concentrated to obtain 54.99 g of crude intended product having a purity of 76.8% and containing 16.4% of the solvent. The yield was 98%.

The crude product had a sufficient purity as an intermediate so that it was provided without purification for the subsequent step. An analysis sample was obtained by concentrating the crude product for removal of the solvent, and the physical properties and spectrum data of the intended product thus obtained are shown below.

(E)-2-Isopropyl-5-methyl-2,4-hexadienol (3)

Colorless Liquid

GC-MS (EI, 70 eV): 27, 43, 55, 69, 81, 93, 111 (base peak), 123, 139, 154 (M+).

IR (D-ATR): ν=3326, 2962, 2924, 2871, 1652, 1615, 1447, 1379, 1362, 1077, 1060, 1043, 996 cm$^{-1}$.

$^1$H-NMR (500 MHz, CDCl$_3$): δ=1.08 (6H, d, J=7.3 Hz), 1.77 (3H, s), 1.81 (3H, s), 2.95-3.04 (1H, m), 4.16 (2H, s), 6.08 (1H, dt, J=11.5, 1.3 Hz), 6.20 (1H, d, J=11.5 Hz) ppm.

$^{13}$C-NMR (125 MHz, CDCl$_3$): δ=18.10, 21.38 (2C), 26.49, 28.07, 64.36, 119.90, 121.15, 135.81, 143.18 ppm.

Example 12

Synthesis of
(E)-2-isopropyl-5-methyl-2,4-hexadienyl acetate (4)

In a nitrogen atmosphere, 60.0 g of acetic anhydride was added dropwise over 5 minutes to a mixture of 54.9 g of 2-isopropyl-5-methyl-2,4-hexadienol (3) being obtained in Example 11 and having a purity of 76.8%, 56.0 g of pyridine, and 300 ml of acetonitrile, which was stirred under ice cooling. The reaction mixture was stirred under ice cooling for one hour and at room temperature for 17.5 hours, and subjected to addition of ice water, followed by extraction with ethyl acetate. The ethyl acetate solution was subjected to work-up including washing, drying and concentration to obtain 55.84 g of crude intended product.

The crude intended product was distilled under reduced pressure to obtain 47.70 g of the intended product having a purity of from 93.4 to 96.6% which is a lower value than the actual purity due to elimination of acetic acid in GC, and an (E)-isomer purity of from 98.0 to 99.2%. The yield was 75%. The physical properties and spectrum data of the resulting intended product are shown below.

(E)-2-Isopropyl-5-methyl-2,4-hexadienyl acetate (4)

Boiling point: from 101 to 102° C./665 Pa

EI-MS (70 eV): 27, 43, 55, 67, 77, 93, 105, 121 (base peak), 136, 196 ((M+).

CI-MS (70 eV, isobutane): 137 (base peak, (M-AcOH+H)$^+$)

IR (D-ATR): ν=2964, 2929, 2873, 1739, 1651, 1449, 1375, 1357, 1232, 1020 cm$^{-1}$.

$^1$H-NMR (500 MHz, CDCl$_3$): δ=1.05 (6H, d, J=6.9 Hz), 1.76 (3H, s), 1.81 (3H, s), 2.05 (3H, s), 2.96-3.04 (1H, m), 4.59 (2H, s), 6.07 (1H, dt, J=11.5, 1.3 Hz), 6.21 (1H, d, J=11.5 Hz) ppm.

$^{13}$C-NMR (125 MHz, CDCl$_3$): δ=18.16, 21.16, 21.21 (2C), 26.49, 28.07, 66.57, 119.78, 125.10, 137.19, 137.55, 170.84 ppm.

Comparative Example 1

Synthesis of
(E)-2-isopropyl-5-methyl-2,4-hexadienoic acid (2)

(Synthesis Example Through Isomerization with a Sulfur Compound)

In a nitrogen atmosphere, a mixture of 5.0 g of 2-isopropenyl-5-methyl-4-hexenoic acid (1) having an isomer purity of 99.5% and 40 mg of benzenethiol was heated to from 100° C. to 120° C. for 5 hours while being stirred. The reaction mixture was subjected to capillary GC analysis under the similar conditions as in Example. Consequently, the content of 2-isopropenyl-5-methyl-4-hexenoic acid as an isomer in the reaction mixture was 99.6% so that the isomerization hardly proceeded, or progress of the reaction was very slow. Thus, it is evident from the results that it is important to sequentially carry out isomerization with a base and isomerization with a sulfur compound.

The invention claimed is:

1. A method for producing (E)-2-isopropyl-5-methyl-2,4-hexadienyl acetate, comprising the steps of:

isomerizing 2-isopropenyl-5-methyl-4-hexenoic acid represented by formula (1):

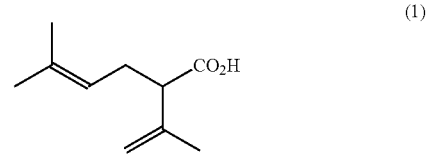

into (E)-2-isopropyl-5-methyl-2,4-hexadienoic acid represented by formula (2):

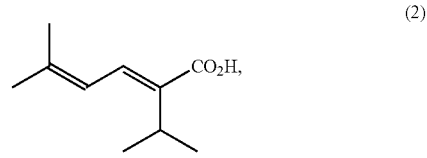

reducing the (E)-2-isopropyl-5-methyl-2,4-hexadienoic acid (2) into (E)-2-isopropyl-5-methyl-2,4-hexadienol represented by formula (3):

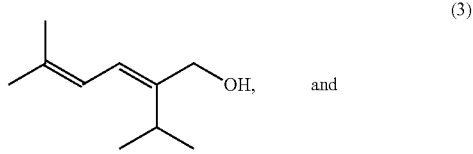

acetylating the (E)-2-isopropyl-5-methyl-2,4-hexadienol (3) into (E)-2-isopropyl-5-methyl-2,4-hexadienyl acetate represented by formula (4):

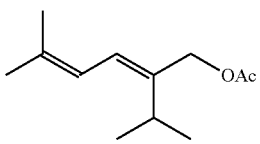

(4)

wherein Ac represents an acetyl group, and
wherein the step of isomerizing comprises isomerizing in the presence of a metal alkoxide, or comprises isomerizing in the presence of the same or different metal alkoxide and subsequently isomerizing in the presence of an organic sulfur compound.

2. The method for producing (E)-2-isopropyl-5-methyl-2,4-hexadienyl acetate according to claim 1, wherein the step of isomerizing further comprises recrystallizing an isomeric mixture obtained by isomerization to isolate thus formed (E)-2-isopropyl-5-methyl-2,4-hexadienoic acid.

3. The method for producing (E)-2-isopropyl-5-methyl-2,4-hexadienyl acetate according to claim 1, wherein the metal alkoxide comprises one or more of sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide.

4. The method for producing (E)-2-isopropyl-5-methyl-2,4-hexadienyl acetate according to claim 1, wherein the organic sulfur compound comprises one or more of elemental sulfur, hydrogen sulfide, thiocyanic acid, methanethiol, ethanethiol, butanethiol, benzenethiol, thiosulfuric acid, thioacetic acid, thioglycolic acid, 3-mercaptopropionic acid, diphenyl sulfide, diphenyl disulfide, butadienesulfone, thioacetamide, thioanisole, and salts thereof.

5. The method for producing (E)-2-isopropyl-5-methyl-2,4-hexadienyl acetate according to claim 1, wherein isomerization proceeds in the presence of a solvent comprising one or more of water, alcohols, ethers, hydrocarbons, aprotic polar solvents, and nitriles.

6. The method for producing (E)-2-isopropyl-5-methyl-2,4-hexadienyl acetate according to claim 2, wherein recrystallization comprises dissolving the isomeric mixture containing (E)-2-isopropyl-5-methyl-2,4-hexadienoic acid in a solvent comprising one or more of water, alcohols, ethers, hydrocarbons, and nitriles.

7. The method for producing (E)-2-isopropyl-5-methyl-2,4-hexadienyl acetate according to claim 1, wherein reducing (E)-2-isopropyl-5-methyl-2,4-hexadienoic acid (2) to (E)-2-isopropyl-5-methyl-2,4-hexadienol represented by formula (3) comprises reducing (E)-2-isopropyl-5-methyl-2,4-hexadienoic acid (2) with a reducing agent selected from the group consisting of hydrogen, boron compounds, metal hydrides, and complex hydrides.

* * * * *